(12) United States Patent
Fairfield et al.

(10) Patent No.: US 9,476,970 B1
(45) Date of Patent: Oct. 25, 2016

(54) CAMERA BASED LOCALIZATION

(75) Inventors: Nathaniel Fairfield, Mountain View, CA (US); Christopher Paul Urmson, Mountain View, CA (US); Michael Steven Montemerlo, Mountain View, CA (US)

(73) Assignee: Google Inc., Mountain View, CA (US)

( * ) Notice: Subject to any disclaimer, the term of this patent is extended or adjusted under 35 U.S.C. 154(b) by 460 days.

(21) Appl. No.: 13/423,704

(22) Filed: Mar. 19, 2012

(51) Int. Cl.
*H04N 7/18* (2006.01)
*G01S 11/12* (2006.01)
*G01S 5/00* (2006.01)
*A61B 5/18* (2006.01)

(52) U.S. Cl.
CPC .............. *G01S 11/12* (2013.01); *A61B 5/18* (2013.01); *G01S 5/0009* (2013.01)

(58) Field of Classification Search
CPC .............. G06K 9/00832; G06T 2207/10016; G06T 3/4053; G06T 5/50; G06T 7/0018; G06T 7/0028; G06T 7/0069; G06T 7/20; G06T 7/2013; G06T 7/2066; G06T 13/80; G06T 15/30; G06T 19/003; G06T 1/00; G06T 2200/32; G06T 2207/10
See application file for complete search history.

(56) References Cited

U.S. PATENT DOCUMENTS

| | | | | |
|---|---|---|---|---|
| 4,802,757 A * | 2/1989 | Pleitner et al. | ................ | 356/2 |
| 5,204,818 A * | 4/1993 | Landecker et al. | .......... | 701/513 |
| 5,550,937 A * | 8/1996 | Bell et al. | .................. | 382/293 |
| 5,606,627 A * | 2/1997 | Kuo | .............. | 382/154 |
| 6,296,317 B1 * | 10/2001 | Ollis et al. | ................ | 299/1.4 |
| 8,098,170 B1 * | 1/2012 | Szczerba et al. | .......... | 340/905 |
| 8,174,568 B2 * | 5/2012 | Samarasekera et al. | ..... | 348/113 |
| 8,229,274 B2 * | 7/2012 | Jeon et al. | .................. | 386/239 |
| 8,606,029 B1 * | 12/2013 | Wong et al. | ................ | 382/239 |
| 8,610,741 B2 * | 12/2013 | Szeliski et al. | .............. | 345/629 |
| 8,644,620 B1 * | 2/2014 | Lam | .............................. | 382/209 |
| 8,666,195 B1 * | 3/2014 | Mierle | .......................... | 382/295 |
| 8,810,599 B1 * | 8/2014 | Tseng | ............................ | 345/633 |
| 8,879,871 B2 * | 11/2014 | Vadon et al. | ................. | 382/285 |
| 8,909,606 B2 * | 12/2014 | Pollack | ......................... | 707/682 |
| 9,043,072 B1 * | 5/2015 | Tisdale | ................. | G05D 1/021 701/28 |
| 2006/0071946 A1 * | 4/2006 | Anabuki et al. | .............. | 345/633 |
| 2006/0160616 A1 * | 7/2006 | Kato et al. | ..................... | 463/30 |
| 2007/0002040 A1 * | 1/2007 | Oldroyd | ........................ | 345/419 |
| 2007/0127101 A1 * | 6/2007 | Oldroyd | ......................... | 359/24 |
| 2007/0171431 A1 * | 7/2007 | Laflamme | .................... | 356/602 |
| 2008/0086464 A1 * | 4/2008 | Enga | ................................ | 707/4 |
| 2008/0089558 A1 * | 4/2008 | Vadon et al. | ................. | 382/113 |
| 2008/0095461 A1 * | 4/2008 | Kim et al. | ..................... | 382/268 |
| 2008/0167814 A1 * | 7/2008 | Samarasekera et al. | ..... | 701/213 |

(Continued)

OTHER PUBLICATIONS

Dellaert et al., Model-Based Car Tracking Integrated With a Road-Follower, Proceedings of the 1998 IEEE International Conference on Robotics & Automation, May 1998, pp. 1889-1894.*

(Continued)

*Primary Examiner* — Tracy Li
*Assistant Examiner* — Mohammad J Rahman
(74) *Attorney, Agent, or Firm* — Lerner, David, Littenberg, Krumholz & Mentlik, LLP (57) ABSTRACT

Aspects of the disclosure relate generally to autonomous vehicles. Specifically, the features described may be used alone or in combination in order to improve the safety, use, driver experience, and performance of these vehicles. In particular, the disclosure includes a system and method of determining a vehicle's location based on a comparison of images captured from the vehicle with a database of images.

24 Claims, 7 Drawing Sheets

(56) References Cited

U.S. PATENT DOCUMENTS

| | | | |
|---|---|---|---|
| 2008/0212838 A1* | 9/2008 | Frigerio | 382/107 |
| 2009/0033753 A1* | 2/2009 | Sato et al. | 348/217.1 |
| 2009/0067725 A1* | 3/2009 | Sasakawa et al. | 382/190 |
| 2009/0201361 A1* | 8/2009 | Lyon et al. | 348/36 |
| 2009/0297063 A1* | 12/2009 | Camp et al. | 382/294 |
| 2010/0008565 A1* | 1/2010 | Chien | G06T 3/00 382/154 |
| 2010/0220173 A1* | 9/2010 | Anguelov et al. | 348/36 |
| 2010/0321490 A1* | 12/2010 | Chen | G01C 11/00 348/118 |
| 2011/0153206 A1* | 6/2011 | Kotaba et al. | 701/208 |
| 2011/0268361 A1* | 11/2011 | Nadabar et al. | 382/182 |
| 2011/0285842 A1* | 11/2011 | Davenport et al. | 348/116 |
| 2011/0299733 A1* | 12/2011 | Jahangir et al. | 382/103 |
| 2012/0051662 A1* | 3/2012 | Naito | 382/275 |
| 2012/0093372 A1* | 4/2012 | Liu | 382/106 |
| 2012/0120069 A1* | 5/2012 | Kodaira et al. | 345/419 |
| 2012/0169513 A1* | 7/2012 | Szczerba et al. | 340/905 |
| 2012/0236024 A1* | 9/2012 | Fujii et al. | 345/620 |
| 2012/0293549 A1* | 11/2012 | Osako | 345/633 |
| 2013/0083201 A1* | 4/2013 | Takacs | 348/169 |
| 2013/0103299 A1* | 4/2013 | Matsuda et al. | 701/300 |
| 2013/0271602 A1* | 10/2013 | Bentley et al. | 348/143 |

OTHER PUBLICATIONS

Noda et al., "Vehicle Ego-Location by Matching In-Vehicle Camera Images to an Aerial Image", ACCV Workshop 2010.*

* cited by examiner

CAMERA BASED LOCALIZATION

BACKGROUND

Autonomous vehicles use various computing systems to aid in the transport passengers from one location to another. Some autonomous vehicles may require some initial input or continuous input from an operator, such as a pilot, driver, or passenger. Other systems, for example autopilot systems, may be used only when the system has been engaged, which permits the operator to switch from a manual mode (where the operator exercises a high degree of control over the movement of the vehicle) to an autonomous mode (where the vehicle essentially drives itself) to modes that lie somewhere in between.

BRIEF SUMMARY OF THE DISCLOSURE

Aspects of the disclosure relate generally to autonomous vehicles. Certain features described below or herein may be used alone or in combination in order to improve the safety, use, driver experience, and performance of these vehicles. Further, any of the features described herein may be used alone or in combination with one or more of the other features described.

In one aspect of the disclosure, the location of a vehicle is determined by capturing a first image of a vehicle's surroundings and accessing a second image, the second image being associated with a location and orientation. The first and second images are then compared, and the location of the vehicle is determined based on the comparison of the first and second image. The vehicle may then be automatically controlled based on the determined location.

In another aspect of the disclosure the first image and second image are projected onto a ground-plane and the ground-plane position of objects with the images are compared. In addition, the ground-plane may be determined based on the vehicle's average position relative to gravity.

In yet another aspect of the disclosure, the first and second images are blurred and are converted to gradient-magnitude images. The two converted images are then convolved in order to compare the two images.

In still another aspect of the disclosure, the second image may be accessed by determining a likely location and orientation of the first image; accessing a database containing a plurality of images, the plurality of images each being associated with a location and orientation; and determining which of the plurality of images has a location and orientation most similar to the likely location and orientation of the first image. The image determined to be the most similar to the likely location and orientation of the first image is then selected as the second image.

In another aspect of the disclosure the plurality of images are arranged within the database in accordance with a spherical geometry hierarchy that is based on the location and orientation of the plurality of images.

In another aspect of the disclosure the second image is one of a plurality of images captured by a camera that is attached to a second vehicle traveling along a predetermined path.

DETAILED DESCRIPTION

Figure 1:
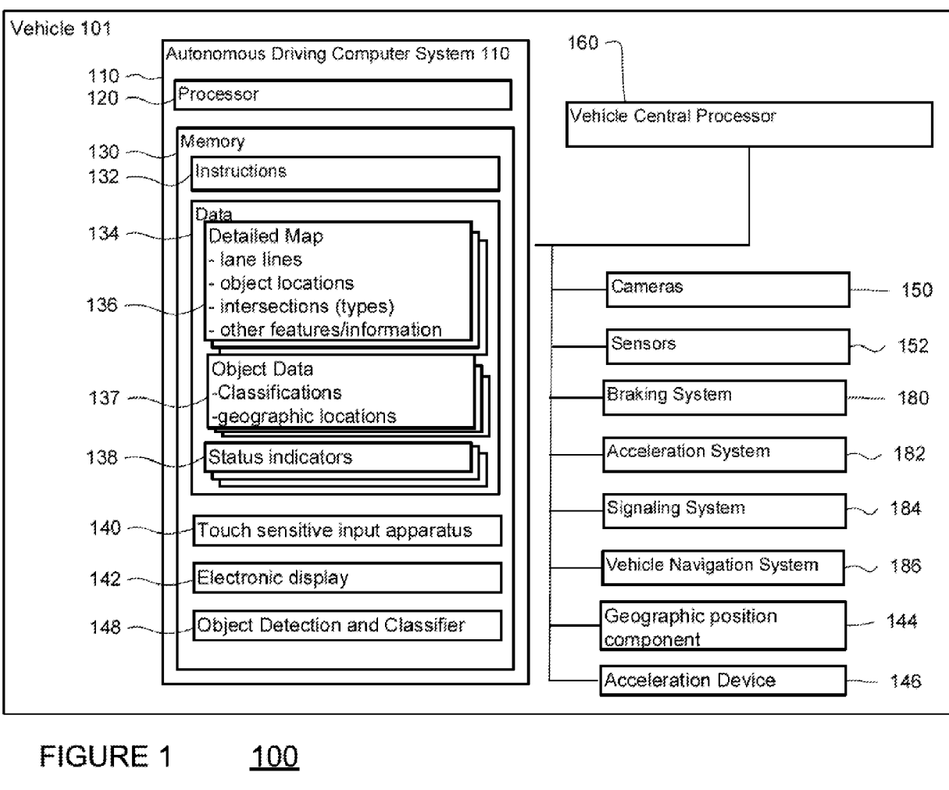
FIG. 1 is a functional diagram of a system in accordance with an aspect of the disclosure.

As shown in FIG. 1, an autonomous driving system 100 in accordance with one aspect of the invention includes a vehicle 101 with various components. While certain aspects of the invention are particularly useful in connection with specific types of vehicles, the vehicle may be any type of vehicle including, but not limited to, cars, trucks, motorcycles, busses, boats, airplanes, helicopters, lawnmowers, recreational vehicles, amusement park vehicles, trams, golf carts, trains, and trolleys. The vehicle may have one or more computers, such as computer 110 containing a processor 120, memory 130 and other components typically present in general purpose computers.

The memory 130 stores information accessible by processor 120, including instructions 132 and data 134 that may be executed or otherwise used by the processor 120. The memory 130 may be of any type capable of storing information accessible by the processor, including a computer-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 132 may be any set of instructions to be executed directly (such as machine code) or indirectly (such as scripts) by the processor. For example, the instructions may be stored as computer code on the computer-readable medium. In that regard, the terms "instructions" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below.

The data 134 may be retrieved, stored or modified by processor 120 in accordance with the instructions 132. For instance, although the system and method is not limited by any particular data structure, the data may be stored in computer registers, in a relational database as a table having a plurality of different fields and records, XML documents or flat files. The data may also be formatted in any computer-readable format. By further way of example only, image data may be stored as bitmaps comprised of grids of pixels that are stored in accordance with formats that are compressed or uncompressed, lossless (e.g., BMP) or lossy (e.g., JPEG), and bitmap or vector-based (e.g., SVG), as well as computer instructions for drawing graphics. The data may comprise any information sufficient to identify the relevant information, such as numbers, descriptive text, proprietary codes, references to data stored in other areas of the same memory or different memories (including other network locations) or information that is used by a function to calculate the relevant data.

The processor 120 may be any conventional processor, such as processors from Intel Corporation or Advanced Micro Devices. Alternatively, the processor may be a dedicated device such as an ASIC. Although FIG. 1 functionally illustrates the processor, memory, and other elements of computer 110 as being within the same block, it will be understood by those of ordinary skill in the art that the processor and memory may actually comprise multiple processors and memories that may or may not be stored within the same physical housing. For example, memory may be a hard drive or other storage media located in a housing different from that of computer 110. Accordingly, references to a processor or computer will be understood to include references to a collection of processors or computers or memories that may or may not operate in parallel. Rather than using a single processor to perform the steps described herein some of the components such as steering components and deceleration components may each have their own processor that only performs calculations related to the component's specific function.

In several of the aspects described herein, the processor may be located remote from the vehicle and communicate with the vehicle wirelessly. In other aspects, some of the processes described herein are executed on a processor disposed within the vehicle and others by a remote processor, including taking the steps necessary to execute a single maneuver.

Computer 110 may all of the components normally used in connection with a computer such as a central processing unit (CPU), memory (e.g., RAM and internal hard drives) storing data 134 and instructions such as a web browser, an electronic display 142 (e.g., a monitor having a screen, a small LCD touch-screen or any other electrical device that is operable to display information), user input (e.g., a mouse, keyboard, touch screen and/or microphone), as well as various sensors (e.g. a video camera) for gathering the explicit (e.g. a gesture) or implicit (e.g. "the person is asleep") information about the states and desires of a person.

The vehicle may also include a geographic position component 144 in communication with computer 110 for determining the geographic location of the device. For example, the position component may include a GPS receiver to determine the device's latitude, longitude and/or altitude position. Other location systems such as laser-based localization systems, inertial-aided GPS, or camera-based localization may also be used to identify the location of the vehicle. The vehicle may also receive location information from various sources and combine this information using various filters to identify a "best" estimate of the vehicle's location. For example, the vehicle may identify a number of location estimates including a map location, a GPS location, and an estimation of the vehicle's current location based on its change over time from a previous location. This information may be combined together to identify a highly accurate estimate of the vehicle's location. The "location" of the vehicle as discussed herein may include an absolute geographical location, such as latitude, longitude, and altitude as well as relative location information, such as location relative to a particular path that the vehicle is to travel.

The device may also include other features in communication with computer 110, such as an accelerometer, gyroscope or another direction/speed detection device 146 to determine the direction and speed of the vehicle or changes thereto. By way of example only, device 146 may determine its pitch, yaw or roll (or changes thereto) relative to the direction of gravity or a plane perpendicular thereto. The device may also track increases or decreases in speed and the direction of such changes. The device's provision of location and orientation data as set forth herein may be provided automatically to the user, computer 110, other computers and combinations of the foregoing.

The computer may control the direction and speed of the vehicle by controlling various components. By way of example, if the vehicle is operating in a completely autonomous mode, computer 110 may cause the vehicle to accelerate (e.g., by increasing fuel or other energy provided to the engine), decelerate (e.g., by decreasing the fuel supplied to the engine or by applying brakes) and change direction (e.g., by turning the front two wheels).

The vehicle may include components for detecting objects external to the vehicle such as other vehicles, obstacles in the roadway, traffic signals, signs, trees, etc. The detection system may include lasers, sonar, radar, cameras or any other detection devices. For example, if the vehicle is a small passenger car, the car may include a laser mounted on the roof or other convenient location. In one aspect, the laser may measure the distance between the vehicle and the object surfaces facing the vehicle by spinning on its axis and changing its pitch. The laser may also be used to identify lane lines, for example, by distinguishing between the amount of light reflected or absorbed by the dark roadway and light lane lines. The vehicle may also include various radar detection units, such as those used for adaptive cruise control systems. The radar detection units may be located on the front and back of the car as well as on either side of the front bumper. These sensors allow the vehicle to understand and potentially respond to its environment in order to maximize safety for passengers as well as objects or people in the environment.

In addition to the sensors described above, the computer may also use input from sensors typical non-autonomous vehicles. For example, these sensors may include tire pressure sensors, engine temperature sensors, brake heat sensors, break pad status, tire tread sensors, fuel sensors, oil level and quality sensors, air quality sensors (for detecting temperature, humidity, or particulates in the air), etc.

Many of these sensors provide data that is processed by the computer in real-time, that is, the sensors may continuously update their output to reflect the environment being sensed at or over a range of time, and continuously or as-demanded provide that updated output to the computer so that the computer can determine whether the vehicle's then-current direction or speed should be modified in response to the sensed environment.

Figure 3:
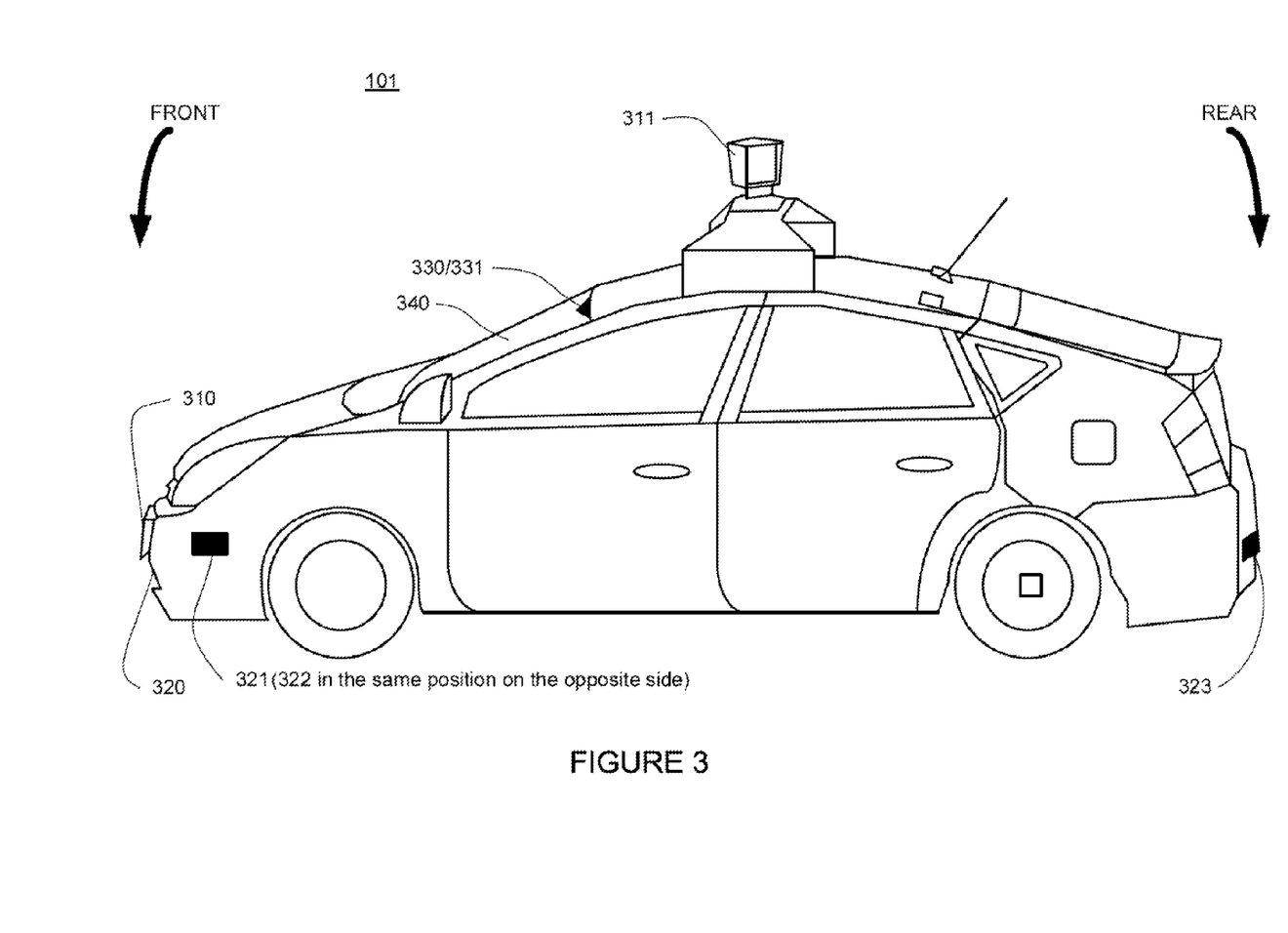
FIG. 3 is a view of the exterior of an exemplary vehicle in accordance with an aspect of the disclosure.

FIG. 3 illustrates a particular embodiment for a small passenger vehicle 101 that includes lasers 310 and 311, mounted on the front and top of the vehicle, respectively. Laser 310 may have a range of approximately 150 meters, a thirty degree vertical field of view, and approximately a thirty degree horizontal field of view. Laser 311 may have a range of approximately 50-80 meters, a thirty degree vertical field of view, and a 360 degree horizontal field of view. The lasers may provide the vehicle with range and intensity information which the computer may use to identify the location and distance of various objects. In one aspect, the lasers may measure the distance between the vehicle and the object surfaces facing the vehicle by spinning on its axis and changing its pitch. Vehicle 101 may include a camera 320 mounted under onto or around the bumper 340. Camera 320 may have various qualities and may be of any type, including panoramic, monocular, or a webcam. In addition, camera 320 may have a range of approximately 200 meters.

In accordance with one embodiment, vehicle 101 uses images obtained from the vehicle's camera to determine the vehicle's current position relative to a desired path of travel. As provided in FIG. 1, camera 150 provides the autonomous driving computer system 110 with data regarding the vehicle's surroundings. For example, the camera 150 is used to take images of the road ahead of vehicle 101. These images may then be processed by the computer system 110 to identify objects that are within the image. Objects may include anything within the vehicle's surroundings, such as buildings, trees, curbs, sidewalks, lane lines, telephone poles, billboards, animals, people, etc. The recorded data may include images, as well as an indication of the image's geographic location and orientation. For example, database 137 may include a library of ground-plane images taken from numerous points along a vehicle's potential route, with each image being tagged with a corresponding location and orientation.

The database of images 137 may be created in any number of ways. In one embodiment, the images contained in database 137 are captured using a camera mounted to a vehicle, similar to the camera 320 on vehicle 101. Specifically, a vehicle's camera may capture images at predefined locations along a predetermined path. For example, images may be taken every meter or every 10 meters that the vehicle travels along the path. These images are then tagged with corresponding location and orientation information and stored within database 137. In this way, the images in database 137 create a map of the predetermined path.

Although FIG. 1 illustrates databases 134, including database 137, as being stored within memory 130, databases 134 may be stored remotely, such as by being accessed on a remote server. In addition, the ground-plane images within database 137 may be stored in a directory hierarchy that allows computer system 110 to quickly access images within the large data set. The directory hierarchy may be based on a spherical geometry library that divides and categorizes regions in into different cell levels. For example, the S2 Spherical Geometry library may be used to divide geographic areas into sub-regions having sides that correspond to 2,300 km, 581 km, 18 km, and 125 m in length. Each region of the S2 library may then be iteratively searched to find the nearest image in terms of both position and heading.

Figure 4:
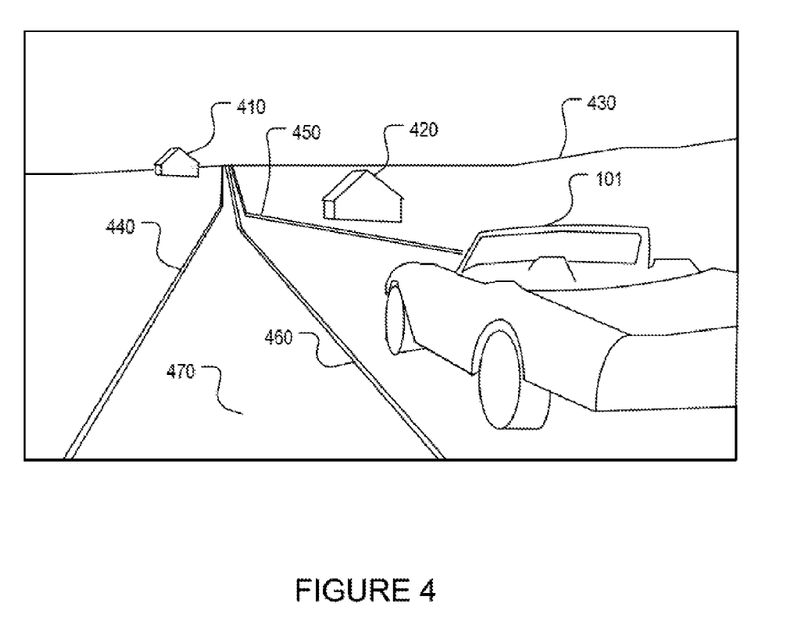
FIG. 4 illustrates an exemplary vehicle setting in accordance with an aspect of the disclosure
Figure 5:
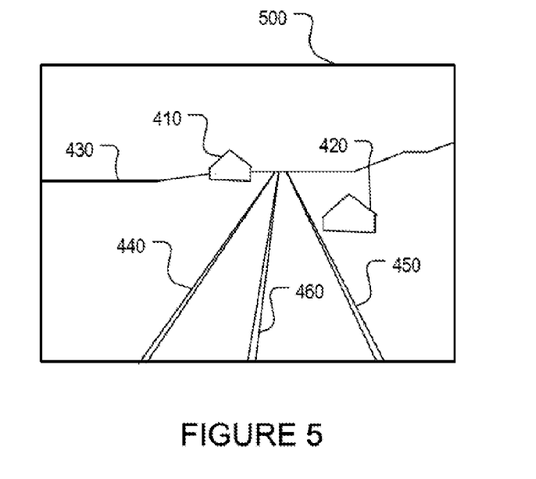
FIG. 5 is an image captured in accordance with an aspect of the disclosure.

FIG. 4 depicts vehicle 101 as it travels on road 470. Along road 470 are objects, such as building 410, building 420, curb 440, curb 450, and lane line 460. In accordance with an aspect of the disclosure, database 137 contains a set of images captured along road 470. Vehicle 101 may use camera 320 to capture image 500 shown in FIG. 5. Computer system 110 may then compare image 500 with the one or more images contained in the map of images stored in database 137. As described below, computer system 110 may then determine the location of the vehicle by identifying the vehicle's relative position compared to the location from which the database image was taken.

In accordance with one embodiment of the disclosure, images taken by vehicle 101 as it travels along a route are compared with the images contained in database 137 by mapping both sets of images to an imaginary ground-plane. The ground-plane represents the two dimensional plane extending out in front of the vehicle that roughly represents the ground over which the vehicle will be traveling. The ground-plane may be defined as the plane along which the vehicle is traveling. Given that vehicle 101 will often traveling along sloped routes, the ground-plane may be defined by the plane created by the vehicle's wheels at any given moment or over a period of time.

Figure 6:
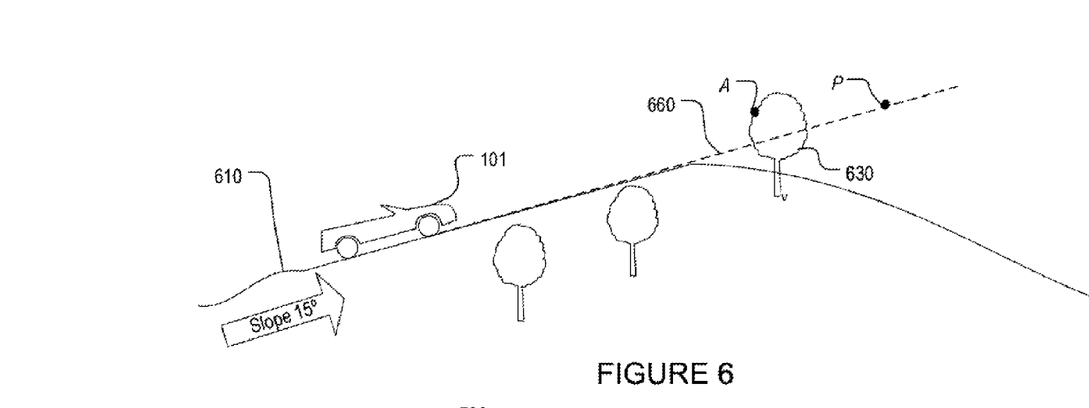
FIG. 6 illustrates an exemplary vehicle setting in accordance with an aspect of the disclosure.

For example, FIG. 6 depicts vehicle 101 traveling along a path having an incline of 15 degrees. In this instance, the ground-plane will have a slope of 15 degrees relative to the horizontal, and will run perpendicular to the figure along the line 660. Sensors may be used to determine the vehicle's attitude, which in turn is used to estimate the ground-plane. In particular, vehicle 101 may collect images from a camera pointed in the direction the vehicle is travelling. As the vehicle drives into the scene captured by the image, sensors on vehicle 101 may be used to determine the roll and pitch of the vehicle, and in turn, determine the slope of the ground-plane associated with each image. In order to remove distortions created by small-scale bumps of the vehicle, the attitude of the vehicle may be filtered to smooth the estimation. For example, vehicle sensors may be used to compute the vehicle's roll and pitch over a period of time, thereby detecting when the vehicle travels over bump 610. Using this data, computer system 110 may determine that the region around bump 610 is not flat, and may therefore reject or filter the data representing the vehicle's attitude while traveling over this region.

Figure 7:
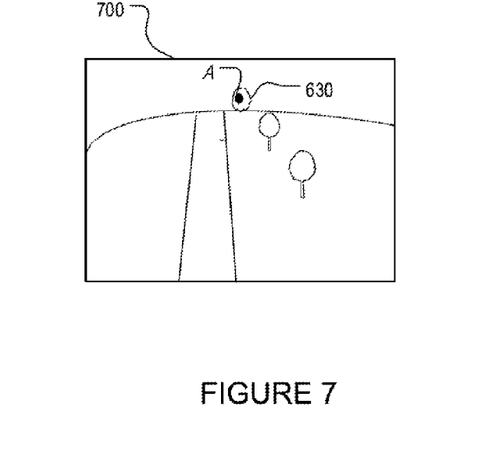
FIG. 7 is an image captured in accordance with an aspect of the disclosure.

Once vehicle 101 has determined the appropriate ground-plane, the image taken by the camera of vehicle 101 may be projected onto the ground-plane so that every pixel within the image corresponds with a particular point on the imaginary ground-plan. The camera's location and angle on the vehicle is taken into account so that the image's field of view can be compared and calibrated with the ground-plane. Given a particular angle and location of vehicle's camera, the computer system 110 may perform a linear correlation between points on a two dimensional image and positions along the ground-plan. For example, Vehicle 101 in FIG. 6 may capture camera image 700 depicted in FIG. 7. Image 700 may be represented as a two dimensional grid of pixels, with each pixel representing a unique location $\{x, y\}$ on the image grid. In projecting image 700 onto the ground-plan, the pixel $\{x, y\}$ is mapped to a corresponding point $\{u, v\}$ on ground-plane. As shown in FIG. 6, Point A on tree 630 is mapped to point P on the imaginary ground-plane 660.

In projecting an image onto the ground-plane, computer system 110 may take account of the various attributes of the camera used to capture the image. For example, computer system 110 may adjust for any radial distortion in the camera's lens, as well as the position and orientation of the camera on the vehicle itself. In addition, images taken by the vehicle during hard turns will often not provide useful information. Accordingly, these images may be discarded. In some circumstances the vehicle will be localized based on images that were captured several seconds in the past. In that instance, a short-term dead-reckoning trajectory may be used in order to fill the gaps in the estimated vehicle position.

In accordance with one embodiment of the disclosure, computer system 110 may access a sequence of ground-plane images contained in database 137 that correspond to the path along which vehicle 101 is traveling. In order to determine the general location of the vehicle, vehicle 101 may use a geographic position component 144, such as a GPS system. The GPS system may provide computer system 110 with a number of points representing the vehicle's approximate geographic position. Typically, each of these points will be within 100 meters of the vehicle's actual position. Computer System 110 may select on or more of these approximate locations and access a database image that is tagged with a geographic location closest to the selected location. Computer system 110 may then compare the offset between the selected database image and a current image taken by camera 320 so as to determine the vehicles exact location. Alternatively, computer system 110 may remove some of the approximate locations from consideration as being incorrect.

Figure 8:
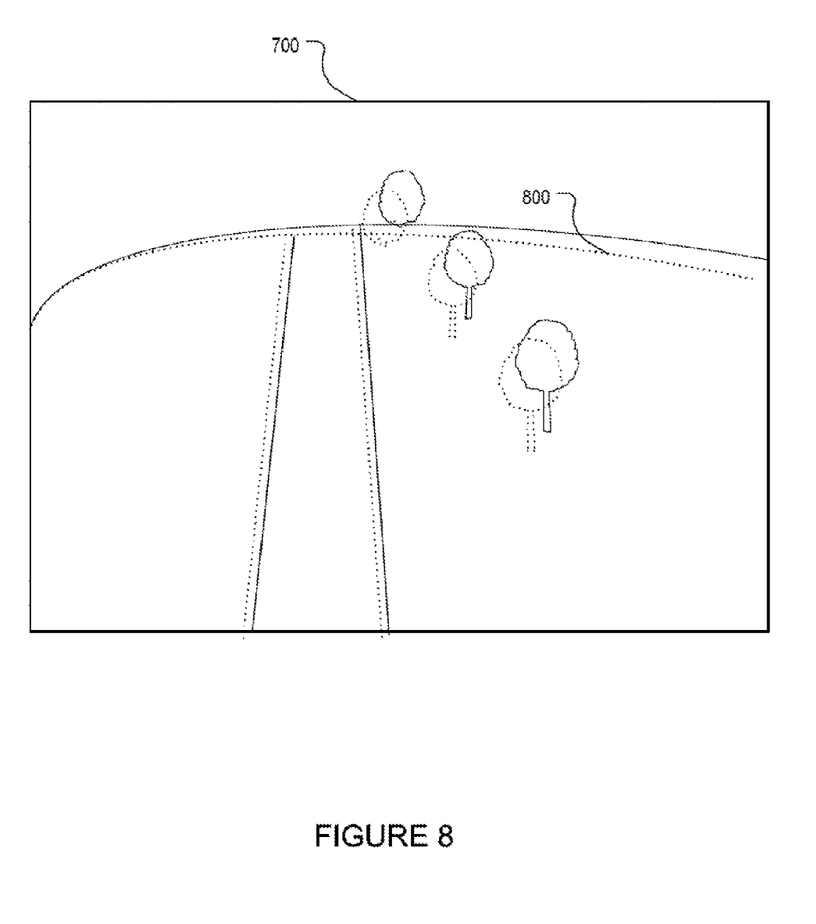
FIG. 8 is an example of image offset in accordance with an aspect of the disclosure.

In one embodiment, a convolution score for the database image and camera image may be determined by performing a region-by-region (e.g., pixel-by-pixel) comparison between the two images. For example FIG. 8 shows a ground-plane camera image 700 of FIG. 7 (shown as with solid lines) overlaid with a ground-plane database image 800 (shown with dotted lines) at an offset. Computer system 110 may compare each pixel from image 700 with the corresponding overlaid pixel from image 800 by, for example, multiplying together each pair of overlaid pixel values. The resulting products may be summed to determine a score. A convolution score may be determined using the same pixel-by-pixel comparison. Computer system 110 may then compare the resulting convolution scores to determine which offset more accurately estimates the shift between images 700 and 800.

In the same way, a multitude of convolution scores between two images may be determined using a fast Fourier transform (FFT), such as, for example, the Cooley-Tukey FFT. Alternatively, any number of available FFT's in the publicly available FFTW library could be used. For example, processor 120 may perform an FFT for each of the two images, multiply the FFT results together, and perform an inverse FFT on the product. These operations result in a score image—where the pixels of a score image represent a convolution score for a particular offset. These score image pixels may be addressable using a coordinate system. For example, the top-left pixel of an image may be represented by the coordinates (0,0). Moreover, the pixels immediately to the right and immediately below pixel (0,0) may, for example, have the coordinates (1,0) and (0,1), respectively. As such, each pixel may be addressable by its coordinates.

The (n, m) pixel of a score image may represent a convolution score of two images where one image is shifted n pixels horizontally and m pixels vertically. For example, the top-left pixel (e.g., pixel (0,0)) of a score image may represent the convolution score of two images overlaid without an offset. Similarly, the pixel immediately to the right of the top-left pixel (e.g., pixel (1,0)) of the score image may represent, for example, the convolution score of two images with one image shifted horizontally by one pixel.

Returning to FIG. 8, computer system 110 may determine a score image for images 700 and 800 by performing an FFT on each image, multiplying together the results of the FFTs, and taking the inverse FFT of the product. The score image may then be analyzed to determine the shift between the two images. For example, the convolution of images 700 and 800 may determine that image 700 is shifted 46 pixels to the right and 98 pixels up from image 800. Since both of the images have been projected onto the ground-plane, computer system 110 may translate the shift in image pixels into a shift in position. Specifically, computer system 110 may determine where vehicle 101 was positioned—relative to the location of image 800—when it took image 700.

In performing the image convolution, the images may be blurred and then converted to gradient-magnitude images. The blurring of the images reduces the effects of both high-frequency noise, as well as range-dependent detail. By converting the images to gradient-magnitude images, the edges of objects of objects can be identified in that it is at the edge of an object that the image brightness changes sharply. In addition, the gradient-magnitude images reduce the impact of illumination effects. For example, gradient-magnitude images allows computer system 110 to more easily match the edges of objects contained in a database image that was taken on a cloudy day or at night, with the camera image that is taken on a sunny day. While changes in shadows may create differences between two—otherwise identical—gradient-magnitude images, the shadows will not change the gradient-magnitude value for most of the objects within the image. Accordingly, a match between the two images may still be accomplished. However, in order to further reduce illumination effects, the images stored within database 137 are preferably captured on cloudy days that have minimum shadows.

Once the ground-plane database image and the ground-plane camera image are convolved, computer system 110 will be able to identify the degree in which the edges of objects shown in both images overlap. Specifically, the convolution will allow computer system 110 to identify the areas on the projected ground-plane in which the pixels of both images contain the same, or similar, gradient-magnitude values. In turn, any offset between the database image and the vehicle's camera image will indicate an offset of the vehicle's current location relative to the location from which the database image was taken.

In one embodiment, computer system 110 may use multiple camera images taken sequentially from vehicle 101 and compare these images with one or more database images to determine the vehicles current location. As described above, a GPS system might provide a number of potential locations for the vehicle over, for example, a 100 meter radius. As the vehicle travels along a path, computer system 110 may compare current images with database images to continually refine the estimated vehicle location. For example, computer system may use a particle filter to eliminate those estimated positions that do not match well with the image comparisons that are being performed. In this example, each particle represents a hypothetical position of vehicle 101. In addition, computer system 110 may weight and resample particles based on the degree to which the particles match the image convolution data.

Figure 2:
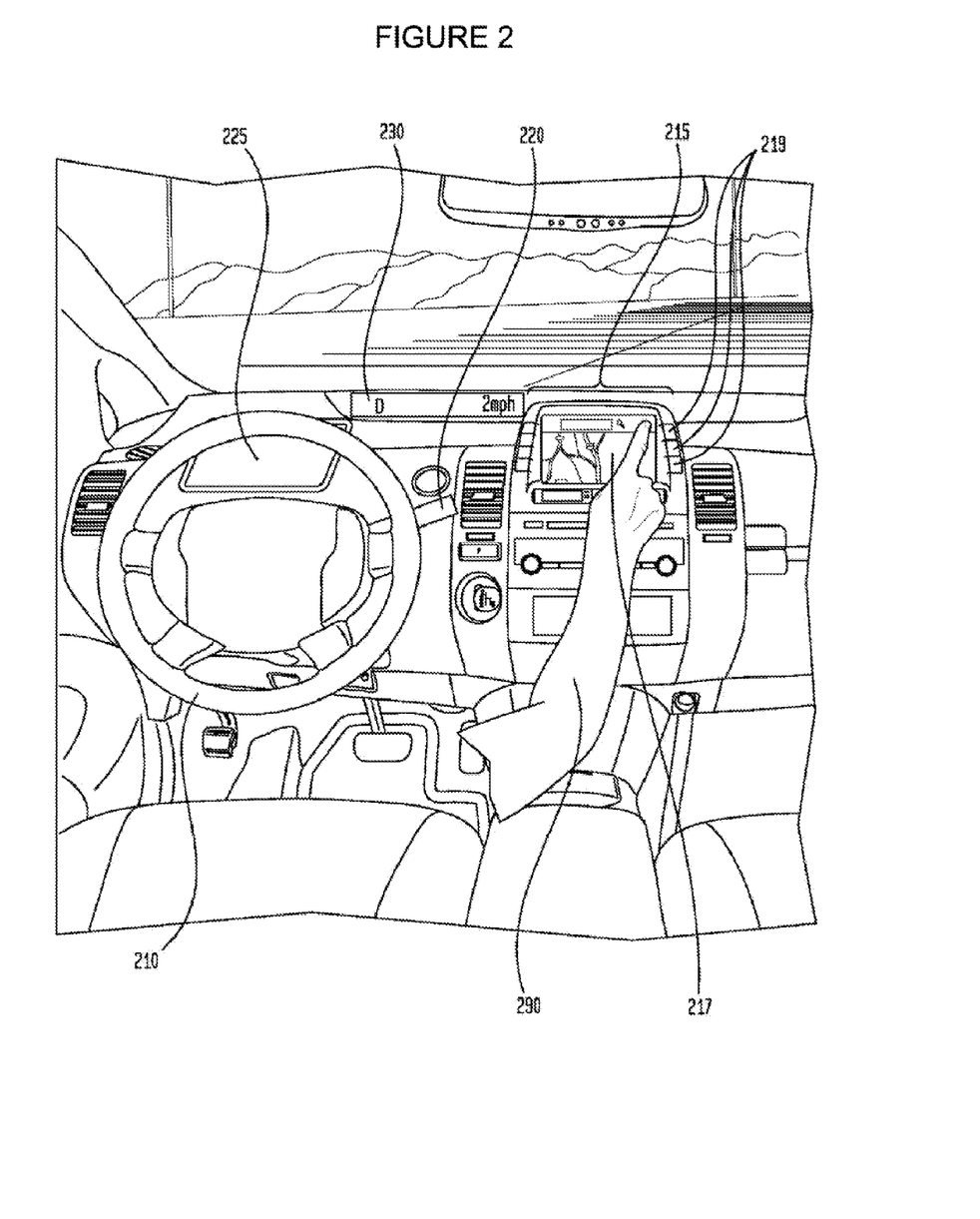
FIG. 2 is an exemplary design of the interior of an autonomous vehicle in accordance with an aspect of the disclosure.

Computer 110 may use visual or audible cues to indicate whether computer 110 is obtaining valid data from the various sensors, whether the computer is partially or completely controlling the direction or speed of the car or both, whether there are any errors, etc. Vehicle 101 may also include a status indicating apparatus, such as status bar 230, to indicate the current status of vehicle 101. In the example of FIG. 2, status bar 230 displays "D" and "2 mph" indicating that the vehicle is presently in drive mode and is moving at 2 miles per hour. In that regard, the vehicle may display text on an electronic display, illuminate portions of vehicle 101, or provide various other types of indications. In addition, the computer may also have external indicators which indicate whether, at the moment, a human or an automated system is in control of the vehicle, that are readable by humans, other computers, or both.

In one example, computer 110 may be an autonomous driving computing system capable of communicating with various components of the vehicle. For example, computer 110 may be in communication with the vehicle's conventional central processor 160 and may send and receive information from the various systems of vehicle 101, for example the braking 180, acceleration 182, signaling 184, and navigation 186 systems in order to control the movement, speed, etc. of vehicle 101. In addition, when engaged, computer 110 may control some or all of these functions of vehicle 101 and thus be fully or merely partially autonomous. It will be understood that although various systems and computer 110 are shown within vehicle 101, these elements may be external to vehicle 101 or physically separated by large distances.

Using this offset information, computer system 110 may then automatically control vehicle 101 as it travels along a particular path. In one embodiment, a driver could manually drive vehicle 101 along a predetermined path from one location to another. While being manually driven, the vehicle's camera may capture and store images along the traveled path that may later be used to autonomously control the vehicle along the same path. For example, vehicle 101 and the vehicle's computer 110 may implement all or part of diagram 900 shown in FIG. 9. As provided in diagram 900, the vehicle is driven manually along one or more paths (Block 910). While traveling along the paths, a camera associated with the vehicle captures images of the vehicle's surroundings (Block 920). The captured images are tagged with data indicating the images' location and orientation (Block 930) and are then stored in a database, such as database 137 (Block 940).

Figure 9:
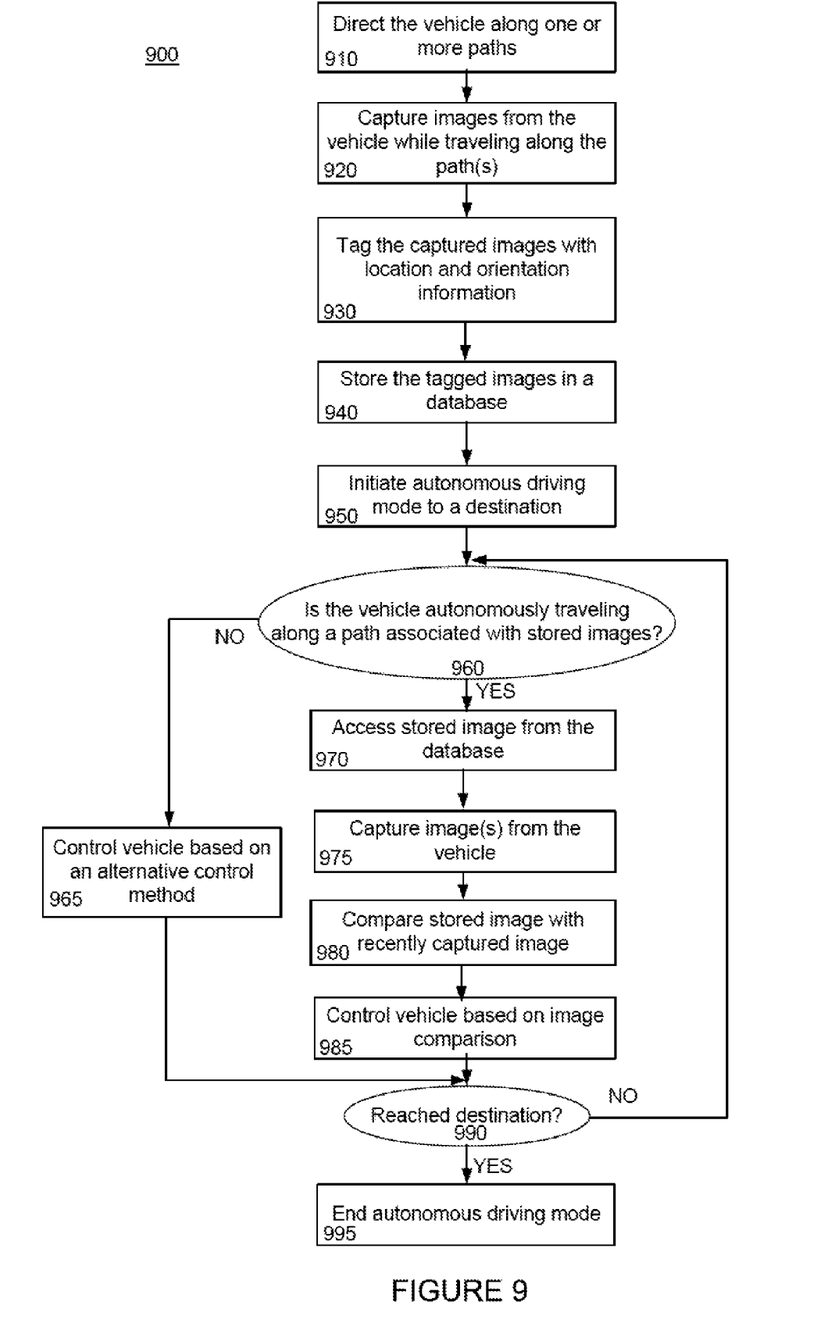
FIG. 9 is a diagram in accordance with an aspect of the disclosure.

The vehicle is then switched to autonomous driving mode so as to travel to a particular destination, or along a particular path (Block 950). The vehicle's computer may then determine whether the path along which it is autonomously traveling corresponds to a path for which images have previously been captured and stored (Block 960). If the current path of travel is the same as a path for which images have been stored, the vehicle may access one or more of the stored images from the database (Block 970). The accessed image should roughly correspond to the vehicle's current position along the path. The vehicle may then use it's camera to capture an image, or images, of the vehicles surroundings (Block 975). The vehicle's computer then compares the recently captured image with the accessed database image (Block 980). As described above, the comparison between the two images may include projecting each of the images along an imaginary ground-plane and then convolving the two images together. The relative position of objects within the convolved images may then be used to determine the current vehicle's position and orientation relative to what the vehicle's position and orientation was when the stored database image was originally captured. Accordingly, the vehicle's computer may autonomously control the vehicle based on the image comparison and maintain the vehicles trajectory along the traveled path (Block 985). For example, the vehicle's computer may determine that in order to stay on the desired path, the vehicle will need to make a 90 degree right turn in 20 meters, and then control the vehicle so that the right turn is made. If the vehicle computer determines that it has reached its destination (Block 990), then it may stop the autonomous driving mode (Block 995). Otherwise, the vehicle may continue to determine whether it is traveling along a path associated with stored images and repeat the process at Block 960. As shown in Block 965, the vehicle may use alternative control methods if it is determined in Block 960 that database images are not available for the path that is currently being traveled.

It should be appreciated that the initiation of the autonomous driving mode in block 950 may occur long after the Blocks 910 through 940 are performed. For example, the vehicle may perform Block 910 through Block 940 by capturing and storing images while a user drives the vehicle from home to work. These stored images may then be used on a later date to autonomously drive the vehicle from the user's home to work in accordance with Block 960 through Block 995. It should also be appreciated that diagram 900 may be performed whole or in part, with certain blocks being omitted or performed in a different order. For example, in one embodiment, vehicle 101 may have access to a database of stored images that were taken by other vehicles or devices. Accordingly, vehicle 101 may perform Block 950 through Block 990 without having previously traveled along the particular path that is being traveled.

In some instances, the images captured by vehicle 101 will be partially obscured by moving objects, such as other cars, trucks, or pedestrians. In this instance, an image captured by vehicle 101 may only partially match an image stored in database 137, in that the moving object will not be present in the database image, or vice versa. Accordingly, the navigation system 100 may be configured to identify overlap in only a portion of an image, while discarding the non-overlapping portion. For example, vehicle sensors may be used to identify nearby moving objects, and computer 110 may be configured to eliminate from consideration any portion of an image that corresponds to the moving object.

In addition, objects that are farther away from vehicle 101 will be projected onto a larger portion of the ground-plane than objects that are closer to vehicle 101. This, in turn, causes objects that are farther away from the vehicle to produce a less accurate ground-plane comparison. Accordingly, the navigation system 100 may be configured to only compare the portion of the two images containing objects that are relatively close to vehicle 101. For example, computer 110 may use only the bottom half of image 500, shown in FIG. 5, when comparing that image with an image stored in the vehicle's database.

FIG. 2 depicts an exemplary design of the interior of an autonomous vehicle. The autonomous vehicle may include all of the features of a non-autonomous vehicle, for example: a steering apparatus, such as steering wheel 210; a navigation display apparatus, such as navigation display 215; and a gear selector apparatus, such as gear shifter 220. Computer 110 may also control status indicators 138, in order to convey the status of the vehicle and its components to a passenger of vehicle 101. For example, vehicle 101 may be equipped with a display 225 for displaying information relating to the overall status of the vehicle, particular sensors, or computer 110 in particular.

Vehicle 101 may include one or more user input devices that enable a user to provide information to the autonomous driving computer 110. For example, a user, such as passenger 290, may input a destination (e.g., 123 Oak Street) into the navigation system using touch screen 217 or button inputs 219. In another example, a user may input a destination by identifying the destination. In that regard, the computer system may extract the destination from a user's spoken command (e.g., by stating or inputting "De young museum" as in the example of FIGS. 2 and 3).

The vehicle may also have various user input devices for activating or deactivating one or more autonomous driving modes. In some examples, the driver may take control of the vehicle from the computer system by turning the steering wheel, pressing the acceleration or deceleration pedals. The vehicle may further include a large emergency button that discontinues all or nearly all of the computer's decision-making control relating to the car's velocity or direction. In another example, the vehicle's shift knob may be used to activate, adjust, or deactivate these autonomous modes.

Computer 110 may include, or be capable of receiving information from, one or more touch sensitive input apparatuses 140. For example, computer 110 may receive input from a user input apparatus and use this information to determine whether a passenger is in contact with, such as by holding or bumping, a particular portion of vehicle 110. The touch sensitive input apparatuses may be any touch sensitive input device capable of identifying a force, for example a force resistance tape may be calibrated to accept or identify a threshold pressure input (such as 10 grams of pressure) or a range of pressures (such as 5-20 grams of pressure).

Again, these inputs may be understood by the computer as commands by the user to, for example, enter into or exit from one or more autonomous driving modes. For example, if the vehicle is being operated in an autonomous mode and the driver bumps the steering wheel, if the force is above the threshold input, the vehicle may go from an autonomous mode to a semi-autonomous mode where the driver has control of at least the steering.

When the driver is ready to relinquish some level of control to the autonomous driving computer, the user may arm the computer. The computer may be armed, for example, by pressing a button or by manipulating a lever such as gear shifter 220. Rather than taking control immediately, the computer may scan the surroundings and determine whether there are any obstacles or objects in the immediate vicinity which may prohibit or reduce the ability of the vehicle to avoid a collision. In this regard, the computer may require that the driver continue controlling the vehicle manually or with some level of control (such as the steering or acceleration) before entering into a fully autonomous mode.

Once the vehicle is able to maneuver safely without the assistance of the driver, the vehicle may become fully autonomous and continue to the destination. It will be understood that the driver may continue to assist the vehicle by controlling, for example, steering or whether the vehicle changes lanes, or the driver may take control of the vehicle immediately in the event of an emergency.

The vehicle may continuously use the sensor data to identify objects, such as traffic signals, people, other vehicles, and other objects, in order to maneuver the vehicle to the destination and reduce the likelihood of a collision. The vehicle may use the map data to determine where traffic signals or other objects should appear and take actions, for example, by signally turns or changing lanes.

Once the vehicle has arrived at the destination, the vehicle may provide audible or visual cues to the driver. For example, by displaying "You have arrived" on one or more of the electronic displays.

The vehicle may also park itself. For example, the map information may include data describing the location of parking spots along a roadway or in a parking lot. The computer may also be configured to use its sensors to determine potential parking spots, such as causing the vehicle to travel down a road and checking for painted lines along a street that indicate an open parking space. If computer determines another vehicle or object is not within the spot (such as by using the object recognition components and methods described above), the computer may maneuver the vehicle into the parking spot by controlling the steering and speed of the vehicle.

The vehicle may also have various parking modes activated by the driver when the driver is leaving the vehicle. For example, the driver may exit the vehicle at a destination and instruct the vehicle to search for parking, circle the block, or continue to another location. The vehicle may, for example, park itself 20 miles away where parking is less expensive or free. Yet further, the vehicles may be placed in a "wait" mode wherein the vehicle does not actually park but rather travels in a continuous loop or to less heavily traveled areas to preserve fuel efficiency. At some predetermined time or when the vehicle has been summoned by the driver, the vehicle may return to the destination.

The vehicle's driver may also select to have the vehicle act cooperatively with other autonomous vehicles. The cooperation may be controlled at least in part by the vehicle's collective computers, a single one of the cooperating computers, or by a remote server to which the cooperating computers relinquish control.

The invention claimed is:

1. A method for localizing a vehicle, the method comprising:
    capturing a first image of a vehicle's surroundings;
    determining, by one or more processors, a roll and pitch of the vehicle at a particular moment in time;
    determining, by one or more processors, an imaginary plane representing a two dimensional plane extending out in front of the vehicle using the roll and pitch of the vehicle such that the roll and pitch of the vehicle corresponds to a slope of the imaginary plane;
    projecting, by the one or more processors, points of one or more objects from within the first image onto the imaginary plane using the slope of the imaginary plane;
    accessing, by the one or more processors, a second image associated with a camera location of the first image and a camera orientation of the first image;
    projecting, by the one or more processors, points of one or more objects from within the second image onto the imaginary plane;
    determining, by the one or more processors, an offset between the first image and the second image based on at least one point projected from the first image onto the imaginary plane and at least one point projected from the second image onto the imaginary plane; and
    determining, by the one or more processors, a location of the vehicle based on the offset between the first image and the second image.

2. A method of claim 1 further comprising, autonomously controlling the vehicle based on the determined location of the vehicle.

3. A method of claim 1, wherein determining the offset of the first image and the second image comprises:
    identifying at least one object that appears in both the first image and second image; and
    determining an offset of the at least one object within the first image and the second image.

4. A method of claim 3, wherein determining the offset of the at least one object comprises determining the position of the at least one object on the imaginary plane.

5. A method of claim 1, further comprising determining the pitch as a relative orientation of the vehicle with respect to gravity.

6. A method of claim 5, wherein the relative orientation of the vehicle is further determined by averaging a plurality of orientations over a period of time.

7. A method of claim 1, wherein determining the offset the first image and the second image comprises:
    blurring the first and second images;
    converting the first and second images to gradient-magnitude images; and
    convolving the gradient-magnitude images.

8. A method of claim 7, wherein only a portion of the first image and a portion of the second image are used to determine the offset.

9. A method of claim 8, wherein accessing the second image comprises:

determining a likely location and orientation of the vehicle;

accessing a database containing a plurality of images, the plurality of images each being associated with a camera location and a camera orientation;

determining which of the plurality of images has a camera location and a camera orientation most similar to the likely location and orientation of the first image; and selecting the image determined to be the most similar to the likely location and orientation of the first image as the second image.

10. A method of claim 9, wherein in the plurality of images are arranged within the database in accordance with a spherical geometry hierarchy that is based on the location and orientation of the plurality of images.

11. A method of claim 1, wherein the second image is one of a plurality of images captured by a camera that is attached to a second vehicle traveling along a predetermined path.

12. A system for controlling a vehicle, the system comprising:

a camera for capturing a first image of a vehicle's surroundings; and a one or more processors operable to:

determine a roll and pitch of the vehicle at a particular moment in time;

determine an imaginary plane representing a two dimensional plane extending out in front of the vehicle using the roll and pitch of the vehicle such that the roll and pitch of the vehicle corresponds to a slope of the imaginary plane;

project points of one or more objects from within the first image onto the imaginary plane using the slope of the imaginary plane;

access a second image, the second image being associated with a camera location of the first image and a camera orientation of the first image;

project points of one or more objects from within the second image onto the imaginary plane;

determine an offset between one or more objects of the first image and one or more corresponding objects of the second image based on at least one point projected from the first image onto the imaginary plan and at least one point projected from the second image onto the imaginary plane; and determine a location of the vehicle based on the offset.

13. The system of claim 12, wherein the one or more processors are further operable to:

identify at least one object that appears in both the first image and second image;

determine a position of the at least one object within the first image and second image; and determine the location of the vehicle based on the difference between the position of the at least one object within the first image and second image.

14. The system of claim 12, wherein the one or more processors are further configured to determine the pitch as a relative orientation of the vehicle with respect to gravity.

15. The system of claim 14, wherein the one or more processors are further operable to determine the relative orientation of the vehicle by averaging a plurality of orientations of the vehicle over a period of time.

16. The system of claim 14, wherein the one or more processors are further operable to:

blur the first and second images;

convert the first and second images to gradient-magnitude images; and convolving the gradient-magnitude images.

17. The system of claim 16, wherein only a portion of the first image and a portion of the second image are compared.

18. The system of claim 17, wherein the one or more processors further operable to:

determine a likely location and a likely orientation of the first image;

access a database containing a plurality of images, the plurality of images each being associated with a camera location and a camera orientation;

determine which of the plurality of images has a camera location and camera orientation most similar to the likely location and the likely orientation of the first image; and select the image determined to be the most similar to the likely location and likely orientation of the first image as the second image.

19. The system of claim 18, wherein in the plurality of images are arranged within the database in accordance with a spherical geometry hierarchy that is based on the camera location and camera orientation of the plurality of images.

20. The system of claim 12, wherein the one or more processors are further operable to autonomously control the vehicle based on the determined location.

21. A method for navigating a vehicle, the method comprising:

capturing a plurality of images along a path;

determining a roll and pitch of a vehicle at a particular moment in time;

determining an imaginary plane representing a two dimensional plane extending out in front of the vehicle using the roll and pitch such that the roll and pitch of the vehicle corresponds to a slope of the imaginary plane;

associating each image in the plurality of images with a camera location and a camera orientation;

projecting one or more objects from within the plurality of images onto the imaginary plane using the slope of the imaginary plane;

storing the plurality of images in a database;

determining that the vehicle is traveling along the path, the vehicle having a position and orientation relative to surrounding objects;

accessing an image from the plurality of images;

identifying a first object within the accessed image, the first object having an imaginary plane position within the accessed image;

determining a location of the vehicle by comparing the imaginary plane position of the first object with the position and orientation of the vehicle relative to the object; and using, by one or more processors, the determined location to navigate the vehicle.

22. A method of claim 21, wherein comparing the imaginary plane position of the object with the position and orientation of the vehicle relative to the object comprises:

capturing a camera image from the vehicle;

projecting the camera image onto the imaginary plane; and comparing the camera image with the accessed image.

23. A method of claim 22, wherein comparing the camera image with the accessed image comprises:

blurring the accessed image and the camera image;

converting the accessed image and the camera image to gradient-magnitude images; and convolving the gradient-magnitude images.

24. The system of claim 18, further comprising the vehicle.

\* \* \* \* \*